(12) United States Patent
Nzike et al.

(10) Patent No.: US 9,999,729 B2
(45) Date of Patent: Jun. 19, 2018

(54) NEEDLE ASSEMBLY ATTACHABLE TO AN INJECTION DEVICE, THE NEEDLE ASSEMBLY HAVING A RESERVOIR ASSEMBLY WITH LOCKING MECHANISM

(71) Applicant: Sanofi-Aventis Deutschland GmbH, Frankfurt am Main (DE)

(72) Inventors: Philippe Nzike, Frankfurt am Main (DE); Michael Schabbach, Frankfurt am Main (DE); Bernd Petermann, Frankfurt am Main (DE); Olaf Zeckai, Weinheim (DE); Meinolf Werner, Worms (DE); Ole Simonowsky, Blankenrath (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 400 days.

(21) Appl. No.: 14/433,610

(22) PCT Filed: Oct. 8, 2013

(86) PCT No.: PCT/EP2013/070880
§ 371 (c)(1),
(2) Date: Apr. 7, 2015

(87) PCT Pub. No.: WO2014/056870
PCT Pub. Date: Apr. 17, 2014

(65) Prior Publication Data
US 2015/0343145 A1    Dec. 3, 2015

(30) Foreign Application Priority Data
Oct. 10, 2012    (EP) .................................... 12187873

(51) Int. Cl.
*A61M 5/31* (2006.01)
*A61M 5/20* (2006.01)
*A61M 5/32* (2006.01)

(52) U.S. Cl.
CPC ........ *A61M 5/2033* (2013.01); *A61M 5/3129* (2013.01); *A61M 5/3294* (2013.01);
(Continued)

(58) Field of Classification Search
CPC .. A61M 2005/3132; A61M 5/20; A61M 5/31; A61M 5/32; A61M 5/2033; A61M 5/3129; A61M 5/3294; A61M 2005/2013
See application file for complete search history.

(56) References Cited

U.S. PATENT DOCUMENTS

| 533,575 A | 2/1895 | Wilkens |
|---|---|---|
| 5,226,895 A | 7/1993 | Harris |

(Continued)

FOREIGN PATENT DOCUMENTS

| CN | 102458518 A | 5/2012 |
|---|---|---|
| CN | 102458522 A | 5/2012 |

(Continued)

OTHER PUBLICATIONS

English Translation of Abstract of Japanese Patent Application No. 2004-107270 dated Oct. 13, 2017.

*Primary Examiner* — Deanna K Hall
(74) *Attorney, Agent, or Firm* — McCarter & English, LLP

(57) ABSTRACT

A reservoir assembly comprising a reservoir housing, a piston, and a locking plug, both movably arranged inside the reservoir housing; wherein the volume between the piston and the locking plug defines a reservoir cavity. The reservoir assembly further comprising a reservoir outlet; and an actuator configured to act on the piston; wherein the locking (Continued)

plug is configured to be movable from a first position to a second position; wherein in the first position the reservoir outlet is not in fluid communication with the reservoir cavity. The reservoir assembly further comprising an interlock configured to prevent movement of at least one of the locking plug and the piston; wherein the interlock having a locked position and an unlocked position.

9 Claims, 8 Drawing Sheets

(52) U.S. Cl.
CPC ............... *A61M 2005/2013* (2013.01); *A61M 2005/3132* (2013.01)

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 8,979,791 B2 | 3/2015 | Davies et al. | |
| 9,352,092 B2 | 5/2016 | Davies et al. | |
| 2002/0052578 A1 | 5/2002 | Moller | |
| 2002/0120235 A1 | 8/2002 | Enggaard | |
| 2002/0138039 A1* | 9/2002 | Hasegawa | A61M 5/1408 604/82 |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2005/0245859 A1 | 11/2005 | Eichhorst | |
| 2006/0153693 A1 | 7/2006 | Fiechter et al. | |
| 2009/0275916 A1 | 11/2009 | Harms et al. | |

FOREIGN PATENT DOCUMENTS

| | | |
|---|---|---|
| EP | 0937471 A2 | 8/1999 |
| EP | 0937476 A2 | 8/1999 |
| EP | 1243280 A2 | 9/2002 |
| EP | 2407194 A1 | 1/2012 |
| EP | 2450072 A1 | 5/2012 |
| FR | 2853836 A1 | 10/2004 |
| JP | 2004107270 A | 4/2004 |
| WO | 9938554 A1 | 8/1999 |
| WO | 0110484 A1 | 2/2001 |
| WO | 2010139675 A1 | 12/2010 |
| WO | 2010139676 A1 | 12/2010 |
| WO | 2012059454 A1 | 5/2012 |

\* cited by examiner

Fig. 3 (Section III-III)

Fig. 6 (Section VI-VI)

NEEDLE ASSEMBLY ATTACHABLE TO AN INJECTION DEVICE, THE NEEDLE ASSEMBLY HAVING A RESERVOIR ASSEMBLY WITH LOCKING MECHANISM

CROSS REFERENCE TO RELATED APPLICATIONS

The present application is a U.S. National Phase application pursuant to 35 U.S.C. § 371 of International Application No. PCT/EP2013/070880 filed Oct. 8, 2013, which claims priority to European Patent Application No. 12187873.0 filed Oct. 10, 2012. The entire disclosure contents of these applications are herewith incorporated by reference into the present application.

FIELD OF INVENTION

The present invention relates to reservoir assemblies, to drug delivery devices, in particular comprising a reservoir adapted to inject a dose of a medicament from that reservoir, and methods for actuating the same.

BACKGROUND

Reservoir assemblies of various types are known in the art, for example vials, prefilled syringes, disposable pen-type injectors, cartridges for reusable injectors, etc. For certain applications it may be necessary to apply tow or more medicaments at the same time. Under certain circumstances, the two medicaments cannot be stored in a single reservoir or container for incompatibility reasons, or the like. Thus, storage in separate reservoirs is necessary. However, it may be required that during administration, the two medicaments from the separate reservoirs be delivered at the same time and in a single injection step.

Co-delivery of two medicaments is known in the art. WO 2010/139676 A1 discloses a medicated module for an injection system to co-deliver at least two medicaments, where a primary delivery device containing a primary medicament accepts a medicated module containing a single dose of a secondary medicament contained within a capsule having an integral flow distributor/distribution system and where both medicaments are delivered through a single hollow needle. The flow distributor may minimize stagnant flow of the medicament and promote/maximize plug flow of the medicament through the capsule and out of the medicated module.

A user of such a system would have to provide the force to expel the primary medicament from the device and the secondary medicament from the capsule of the module. Therefore, the required force may be too high for a user. In addition, the increased pressure may be mistakenly perceived by a user as a malfunction of the system, e.g. an occlusion of the delivery channel.

It is thus an object of the present invention to provide a reservoir assembly, a drug delivery device, and methods for actuating the same, featuring an improved delivery mechanism. It is a further object to provide unambiguous support for a user in handling and/or operating a drug delivery system for co-delivery of at least two medicaments.

SUMMARY

A first aspect of the invention relates to a reservoir assembly comprising a reservoir housing, a piston, and a locking plug, both movably arranged inside the reservoir housing and a biased actuator configured to act on the piston. The volume between the piston and the locking plug defines a reservoir cavity. Further, the reservoir assembly comprises a reservoir outlet to enable at least partly emptying the reservoir cavity. The locking plug is configured to be movable from a first position to a second position, wherein in the first position the reservoir outlet is not in fluid communication with the reservoir cavity. When the locking plug is in the second position, the reservoir outlet is in fluid communication with the reservoir cavity. Further, an interlock is configured having a locked position and an unlocked position. In the locked position, the interlock prevents movement of at least one of the locking plug and the piston. The interlock is configured to allow movement of at least one of the locking plug and the piston, when in the unlocked position.

A reservoir assembly like this has an improved delivery mechanism. The delivery from this kind of reservoir does not require manual force to expel the content of the reservoir. This is provided by the biased actuator. A user would only have to move the interlock from the locking position to the unlocked position in order to enable that the content is expelled. When the interlock is in the locked position, the content of the reservoir would be hermetically sealed because the reservoir outlet is not in fluid communication with the reservoir cavity. Therefore, a reservoir like this would be configured to allow storing, e.g. a liquid medicament, in a ready to use reservoir. Once, the reservoir assembly is about to be used, the interlock is moved from the locked position to the unlocked position to enable expelling the content of the reservoir cavity by means of the biased actuator.

In an embodiment, when the interlock is in the locked position, the reservoir outlet is not in fluid communication with the reservoir cavity. For example, when the interlock is in the locked position the locking plug may seal the reservoir outlet.

In an embodiment, when the interlock is in the unlocked position the locking plug is free to move. The locking plug may be moved to a second position.

In an embodiment, when the locking plug is in the second position, the reservoir outlet is in fluid communication with the reservoir cavity. Preferably, the locking plug is in the second position and the reservoir outlet is in fluid communication with the reservoir cavity when the interlock is in the unlocked position.

In an embodiment, when the interlock is in the unlocked position and the locking plug is in the second position, the reservoir outlet is in fluid communication with the reservoir cavity. For example, the locking plug may be moved to a second position, where it does not seal the reservoir outlet.

In an embodiment, the reservoir assembly further comprises an arrangement to transmit movement of the piston to the locking plug. The reservoir assembly may comprise an arrangement to transfer a force from the piston to the locking plug. Having such arrangement in place, the interlock either interacts with said locking plug or with said piston to prevent movement of at least one of the locking plug and the piston when the interlock is in the locked position. Hence, actuation of the piston by the actuator cannot cause movement of the locking plug, when the interlock is in the locked position. Inversely, actuation of the piston by the actuator may cause movement of at least one of the locking plug and the piston when the interlock is in the unlocked position.

In an embodiment, a fluid may be arranged inside the reservoir cavity. The fluid is substantially incompressible. The fluid may transmit movement of the piston to the locking plug. When the interlock is in an unlocked position, actuation of the piston by the actuator causes movement of the locking plug.

According to an embodiment, the fluid arranged inside the reservoir cavity is the same fluid that shall be expelled from said reservoir arrangement. In particular, the reservoir cavity can be filled with medicament.

In an embodiment, the reservoir assembly may further comprise a head space defined by the locking plug and the housing, wherein when the locking plug is moved into the head space, the locking plug is in the second position. The head space may be empty. The head space may be filled with gas, e.g. air. In one embodiment, the head space is filled with air at ambient pressure. The gas in the head space may provide a pressure to move the locking plug back into the locked position when the reservoir cavity is empty. Alternatively, the head space may comprise a vent to allow gas inside the head space to escape, when the locking plug is in the second position. The head space may be configured to limit the movement of the locking plug. E.g., the head space may comprise protrusions, steps, or the like structures, that engage with the locking plug to stop movement of the locking plug. Alternatively, the gas inside the head space may stop movement of the locking plug.

In one embodiment of a reservoir assembly according to the invention the interlock comprises a movable slider, the slider having an aperture. The actuator comprises a spring and a support element, e.g. a support ring, arranged between the spring and the movable piston. The slider is configured to be moved from a first position to a second position, such that the support ring can pass through the aperture. When the slider is in a position where the support ring can pass through the aperture, the actuator can act on the piston, the piston is movable through the aperture and the locking plug is movable into the second position, so that the reservoir outlet is in fluid communication with the reservoir cavity. A liquid, e.g. a medicament that could be arranged in the reservoir cavity, could then be expelled through the reservoir outlet.

In another embodiment of the reservoir assembly according to the invention, the head space is filled with a liquid and the housing further comprises a sump fluidly separated from the head space. The interlock comprises a slider configured to establish fluid communication between the head space and the sump when the slider is in the unlocked position. The sump could be fluidly separated from the head space by a valve or valve system, or gate. The slider of the interlock is configured to open the valve or valve system, or gate, when the interlock is in the unlocked position. In a preferred embodiment, the headspace and the sump are fluidly separated by a membrane and the slider comprises a tappet configured to pierce the membrane when the slider is in the unlocked position. When the slider is in the unlocked position and the liquid is moved from the head space into the sump, the locking plug is free to be moved into the second position.

Another aspect of the invention relates to a medical device configured for delivering a medicament comprising a reservoir assembly according to the present invention.

A further aspect of the invention relates to a needle assembly attachable to an injection device. The needle assembly comprises a housing having a proximal end and a distal end, wherein the proximal end is configured to be attached to an injection device. A distal needle cannula is fixed at the housing. The housing comprises a reservoir assembly according to the present invention, wherein the reservoir assembly is configured for fluid communication with the distal injection needle. The needle assembly may be in fluid communication with the distal injection needle when the interlock is in the unlocked position.

A housing of a needle assembly may comprise a housing of a reservoir assembly. For example, the housing of the needle assembly could comprise elements that provide wall-like structures that could function as a housing of a reservoir assembly. For example, the housing of the needle assembly could comprise fixing and/or holding elements that provide structure and/or could function as a housing to contain elements of a reservoir assembly. In an embodiment, the housing of the needle assembly comprises a cavity, wherein the inner wall of the cavity defines a reservoir housing. Preferably, the cavity is a cylindrical bore.

Having the housing of the needle assembly comprising a housing of the reservoir assembly would reduce construction complexity and could also reduce cost because less elements are required. Therefore, it would be beneficial to have a needle assembly housing that comprises a reservoir assembly housing.

It is to be noted that all features and embodiments as described herein are to be understood to equally apply to the reservoir assembly, to the drug delivery device as well as to the method of operating the drug delivery device and its reservoir assembly. In particular, a mentioning of a component being configured or arranged to conduct a particular operation is to be understood to disclose a respective method or operation step and vice versa.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

```
H-(Lys)4-des Pro36, des Pro37 Exendin-4(1-39)-NH2,

H-(Lys)5-des Pro36, des Pro37 Exendin-4(1-39)-NH2, des Pro36 Exendin-4(1-39), des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Asp28] Exendin-4(1-39), des Pro36 [IsoAsp28] Exendin-4(1-39), des Pro36 [Met(O)14 Trp(O2)25, Asp28]
Exendin-4(1-39), des Pro36 [Met(O)14 Trp(O2)25, IsoAsp28]
Exendin-4(1-39);
or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Asp28] Exendin-4(1-39), des Pro36 [IsoAsp28] Exendin-4(1-39), des Pro36 [Met(O)14 Trp(O2)25, Asp28]
Exendin-4(1-39), des Pro36 [Met(O)14 Trp(O2)25, IsoAsp28]
Exendin-4(1-39),
``` wherein the group -Lys6-NH2 may be bound to the C-terminus of the Exendin-4 derivative;
or an Exendin-4 derivative of the sequence

```
des Pro36 Exendin-4(1-39)-Lys6-NH2 (AVE0010),

H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2,
```

-continued

H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

Embodiments of the invention will now be described, by way of example only, with reference to the accompanying drawings.

BRIEF DESCRIPTION OF THE DRAWINGS

The figures show:
FIG. 8 is a side and partly section view of the assembly according to FIG. 5 in

DETAILED DESCRIPTION

In the following, embodiments of the present invention will be described with reference to an insulin injection device. The present invention is, however, not limited to such application and may equally well be deployed with injection devices that eject other medicaments, or with other types of medical devices.

Figure 1:
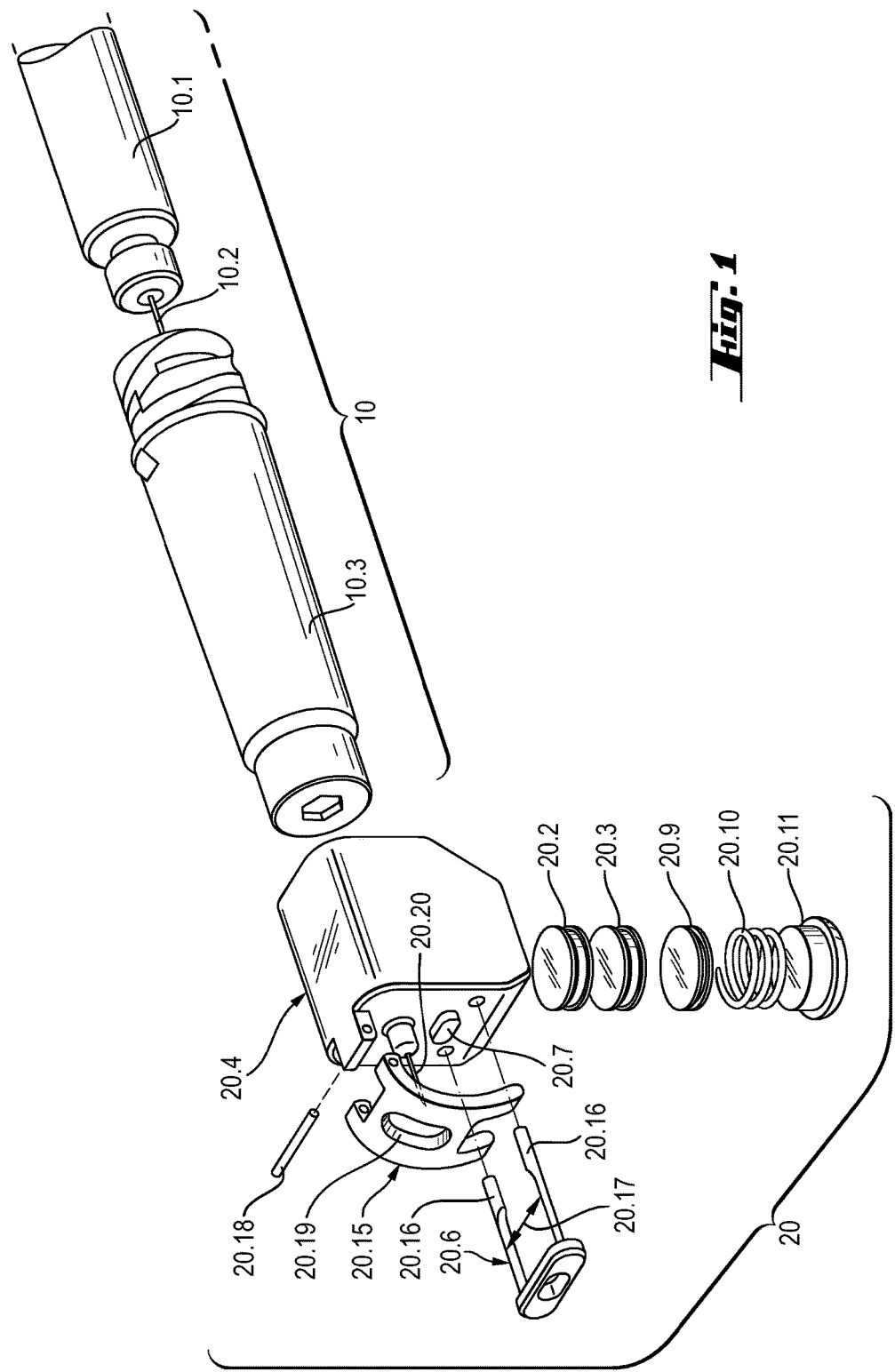
FIG. 1 is an exploded perspective view of an assembly according to the invention.

FIG. 1 shows an exploded perspective view of one embodiment of a reservoir assembly according to the present invention. The reservoir assembly 20.50 (framed by a dotted-dashed line in FIG. 2) is part of a medicated needle assembly 20 that is attachable to an injection device, e.g. a pen-shaped injector.

The injection device 10 of FIG. 1 is a reusable injection pen that comprises an insulin container or vial 10.1 and a holder 10.3 for the vial 10.1, to which a needle 10.2 can be affixed. However, the injection device 10 could be as well a disposable pen having a prefilled container or vial 10.1. In either case, the medicament container 10.1 is closed with a bung on the one end and with a piercable septum or seal (not shown) at the opposite end.

The needle assembly 20 comprises a housing 20.4 that is configured to attach to the injection device 10, e.g. instead of attaching a standard injection needle.

Figure 2:
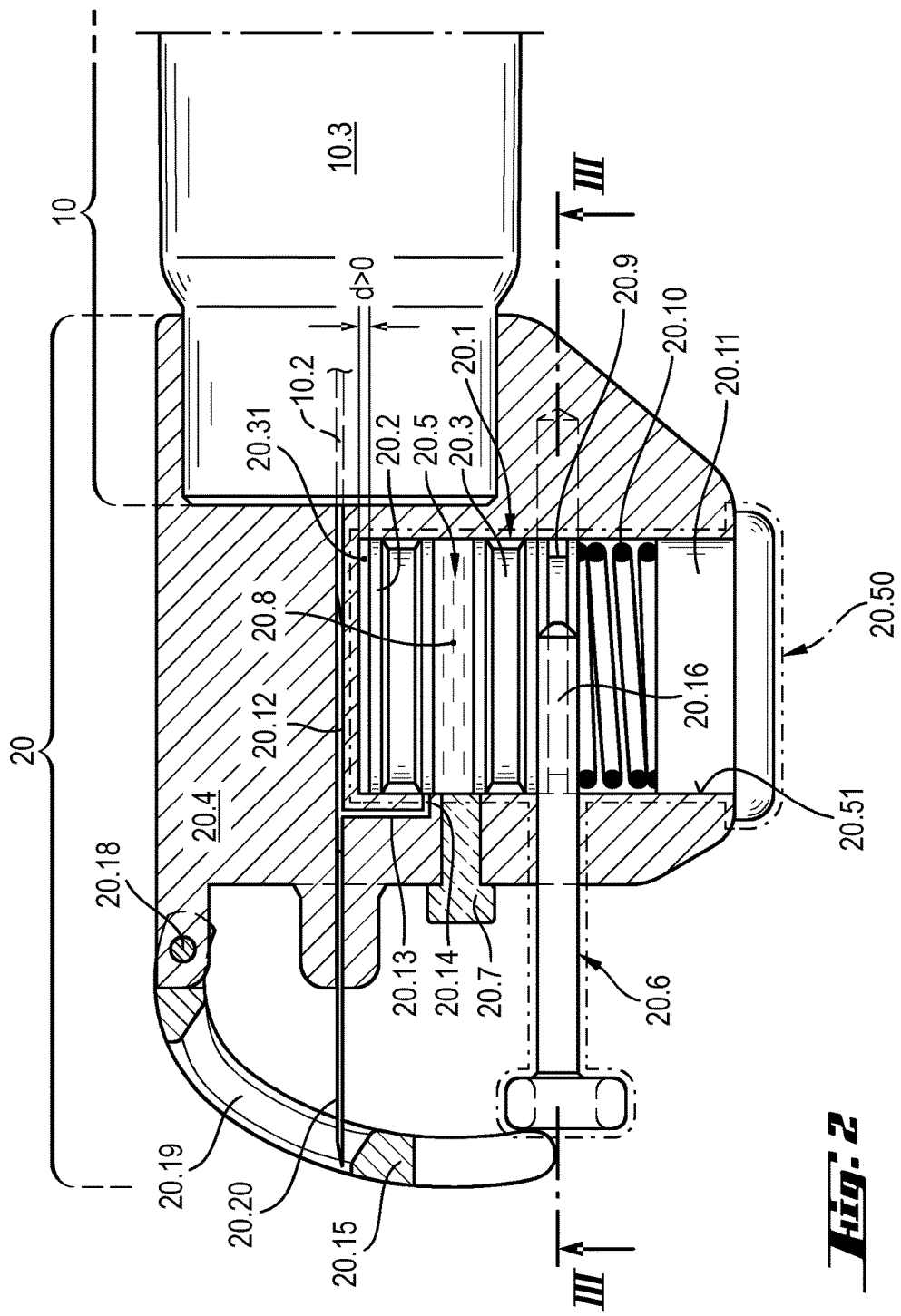
FIG. 2 is a side and partly view of the assembly according to FIG. 1.

As shown in FIG. 2 the housing 20.4 of the needle assembly 20 comprises a reservoir assembly 20.50 (dotted-dashed line) according to the present invention. A chamber or cavity, e.g. a cylindrical bore 20.51, is arranged inside the housing 20.4 accessible from the outside. The inner wall of the bore 20.51 defines a reservoir housing 20.1 containing (from inside to outside) a locking plug 20.2 and a movable piston 20.3, both arranged to be movable inside the cylindrical bore 20.51 and providing a fluid tight sealing with the inner wall of the bore. A reservoir cavity 20.5 is defined between the locking plug 20.2 and movable piston 20.3 which is filled with medicament 20.8. The reservoir assembly 20.50 further comprises a head space 20.31 defined by the locking plug 20.2 and the housing 20.1. Moveable locking plug 20.2 is able to move a distance d into the head space 20.31 until it abuts the end of the cylindrical bore 20.51. Distance d is sufficient for locking plug 20.2 to open outlet 20.14 and fluidly connect the reservoir cavity 20.5 with the outlet 20.14.

Next to the movable piston 20.3 is a support member or support ring 20.9, a spring 20.10, and finally a stopper or closure 20.11 that closes the bore to the outside. The reservoir assembly 20.50 has a reservoir outlet 20.14. The reservoir assembly 20.50 further comprises an interlock 20.6 configured to prevent movement of the moveable locking plug 20.2 and/or the movable piston 20.3. The content of the reservoir cavity, e.g. medicament, can be viewed from outside through an inspection glass 20.7.

FIG. 2 shows a side and partly section view of the needle assembly 20 attached to an injection device 10. A fluid channel 20.12 is arranged inside the housing 20.4 perpendicular to the reservoir housing 20.1 and extends from one end of the housing to the other end, where an injection needle 20.20 is fluidly connected. When the needle assembly 20 is attached to an injection device 10, medicament from the injection device 10 can be discharged through the fluid channel 20.12. The fluid channel 20.12 is fluidly connected to the medicament in the injection device 10 via needle 10.2. The needle 10.2 is attached to or part of the injection device 10. This could be used to prime the injection device 10 by removing air that might be present in the fluid channel 20.12 prior to injection.

In an alternative embodiment (not shown), needle 10.2 is be part of the needle assembly 20 and in fluid communication with the fluid channel 20.12. Needle 10.2 is configured to establish fluid communication to the medicament in the injection device 10 by having a sharp end adapted to pierce a septum of container 10.1.

Returning to the embodiment shown in FIG. 2, a delivery or dispense channel 20.13 inside the needle assembly 20 is configured to establish a fluid communication between the fluid channel 20.12 and the medicament 20.8 inside the reservoir cavity 20.5 of the reservoir assembly 20.50. FIG. 2 shows the reservoir in a locked state, where the reservoir outlet 20.14 is closed or blocked by the movable locking plug 20.2.

Figure 3:
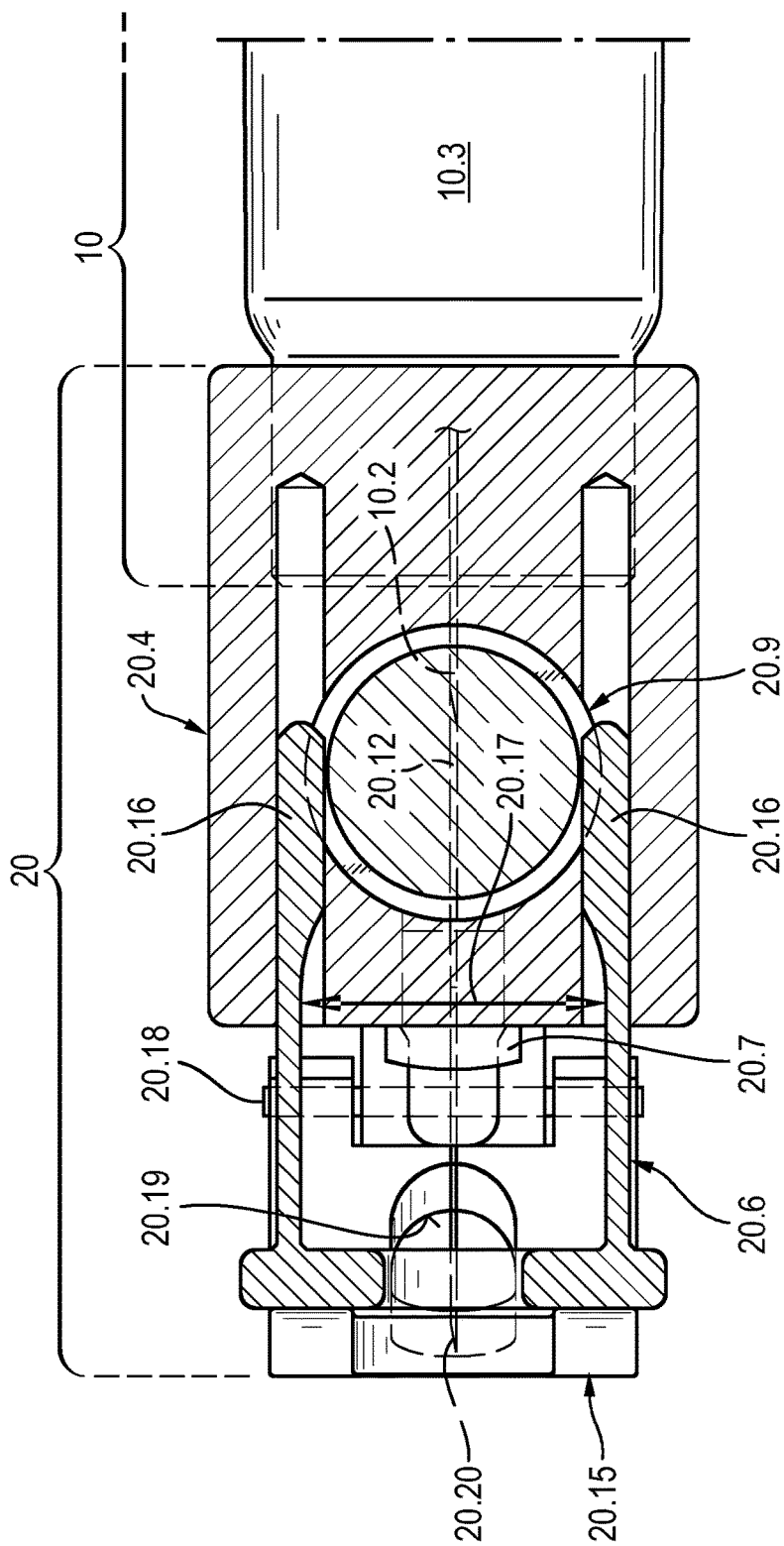
FIG. 3 is a horizontal section view of the assembly according to line III-III in FIG. 2.

FIG. 3 is a horizontal section view according to line III-III in FIG. 2 seen from the top of the needle arrangement 20 showing the interlock 20.6.

In this embodiment the interlock 20.6 is a slider comprising a bar having two legs (20.16, see FIG. 1) extending into the needle arrangement housing 20.4 and reaching the support ring 20.9. The legs 20.16 have a distance sufficient to allow the support ring 20.9 and/or the spring 20.10 to pass through. At their ends the legs 20.16 have extensions configured to engage with the support ring 20.9 when the interlock 20.6 is in a first or locking position. Hence, although biased by spring 20.10 the support ring 20.9 will remain in place and cannot be moved. Also, the movable piston 20.3 as well as the movable locking plug 20.2 is prevented from movement. When the interlock 20.6 is moved towards the arrangement housing 20.4, the legs 20.16 will pass along support ring 20.9, and extensions will disengage the support ring 20.9, which is now free to be moved by the biasing force of spring 20.10. The interlock 20.6 then is in a second or unlocked position and movable piston 20.3 as well as movable locking plug 20.2 is free to move.

Spring 20.10 serves as an actuator exerting a force onto the moveable piston 20.3. Spring 20.10 could alternatively be a compression spring or a gas spring.

The distance of the legs 20.16 forms an aperture 20.17 adapted to allow the support ring 20.9 to pass through. Alternatively, the interlock 20.6 could be a slider comprising a flat solid element having a hole or aperture adapted to allow the support ring 20.9 to pass through.

A user could manually move interlock 20.6 from the locked position to the unlocked position. However, to improve usability, this embodiment features a lever 20.15 having a concave curve towards the arrangement housing 20.4 and is configured to act on the interlock 20.6 which is then transitioned from a locked position to an unlocked position. The lever 20.15 is attached to the housing 20.4 via a hinge 20.18 at one end and abuts the interlock 20.6 at the other end. When the lever 20.15 is moved towards the housing 20.4 the interlock 20.6 will be pushed towards the housing 20.4, such that the extensions of the legs 20.16 disengage from the support ring 20.9. Hence, lever 20.15 is configured to change the status of the interlock 20.6 from locked to unlocked.

In a preferred embodiment, the lever 20.15 could be moved towards the housing 20.4, when a user presses the needle assembly 20 against an injection site. This moves the interlock 20.6 into the unlocked position and the medicament 20.8, which would be located in the reservoir cavity 20.5, can be expelled from the reservoir assembly 20.50 by force of the spring 20.10.

Figure 4:
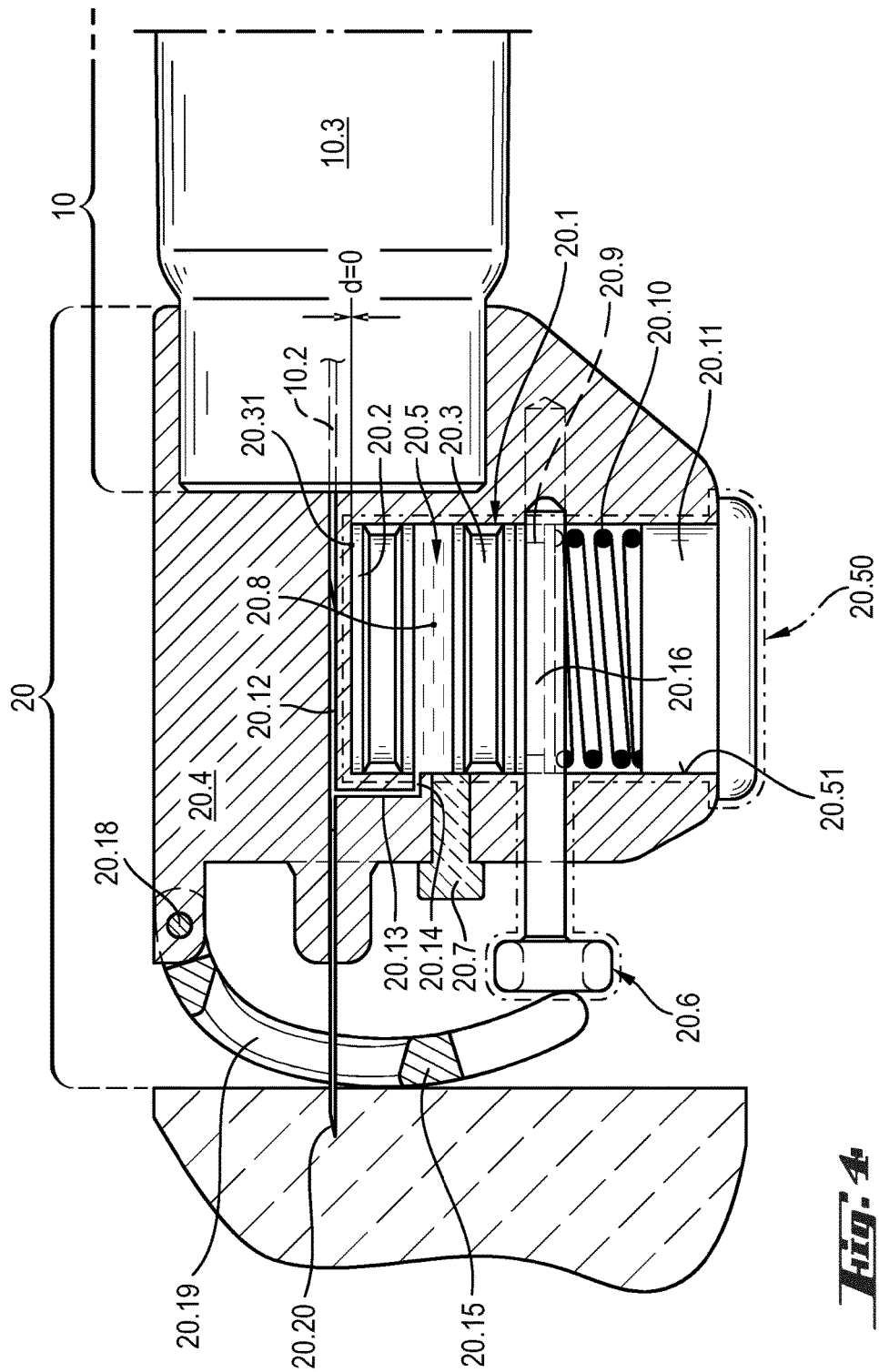
FIG. 4 is a side and partly section view of the assembly according to FIG. 2.

FIG. 4 shows a sectional side view of the needle arrangement 20 where the lever 20.15 is fully depressed and the interlock 20.6 is in an unlocked state. The support ring 20.9 is free to move caused by the biasing force of spring 20.10 as described above. As spring 20.10 acts on the support ring 20.9, support ring 20.9, moveable piston 20.3, medicament 20.8, and moveable locking plug 20.2 will be moved. Moveable locking plug 20.2 is able to move a distance d (see FIG. 2) into a head space 20.31 (see FIG. 2) until it abuts the end of the cylindrical bore 20.51. In this position distance d is zero and, outlet 20.14 is open, and reservoir cavity 20.5 is fluidly connected with outlet 20.14f Alternatively, the bore 20.51 could comprise a step, detent, or the like structure, such that locking plug 20.2 is able to move distance d into the head space 20.31 to open outlet 20.14. In this configuration, locking plug 20.2 would abut the step, detent, or the like structure and would not reach the end of the cylindrical bore 20.51.

As spring 20.10 still presses against support ring 20.9 and movable piston 20.3, medicament will be pushed out the reservoir outlet 20.14, into dispense channel 20.13 and into liquid channel 20.12. Dispense will end when moveable piston 20.3 abuts moveable locking plug 20.2.

Lever 20.15 is configured such that it protects against potential needle stick or reduce needle phobia. For this purpose, lever 20.15 has a cutout 20.19, e.g. of oval shape, to allow an injection needle 20.20 to pass through. Before injection, the injection needle 20.20 tip is shielded by lever 20.15. During injection, a user presses the needle arrangement 20 against an injection site and while lever 20.15 is depressed against the housing 20.4 of the needle arrangement 20 the injection needle 20.20 would extend through the cutout 20.19 and enter the injection site.

As lever 20.15 is depressed the state of the interlock 20.6 is changed and needle arrangement 20 is actuated. Medicament from the needle arrangement 20 is dispensed without the user having to perform a further injecting action, such as depressing a plunger or the like. After the medicament 20.8 is discharged, the user may dispense medicament form the attached drug delivery device 10 in a usual manner. The two medicaments are dispensed subsequently one after the other, without substantial mixing in the device.

According to the construction of the needle assembly 20, the dispense channel 20.13 and the liquid channel 20.12 are configured to minimize ullage and thus help the user to receive the required amount of medicament without wasting medicament.

Figure 5:
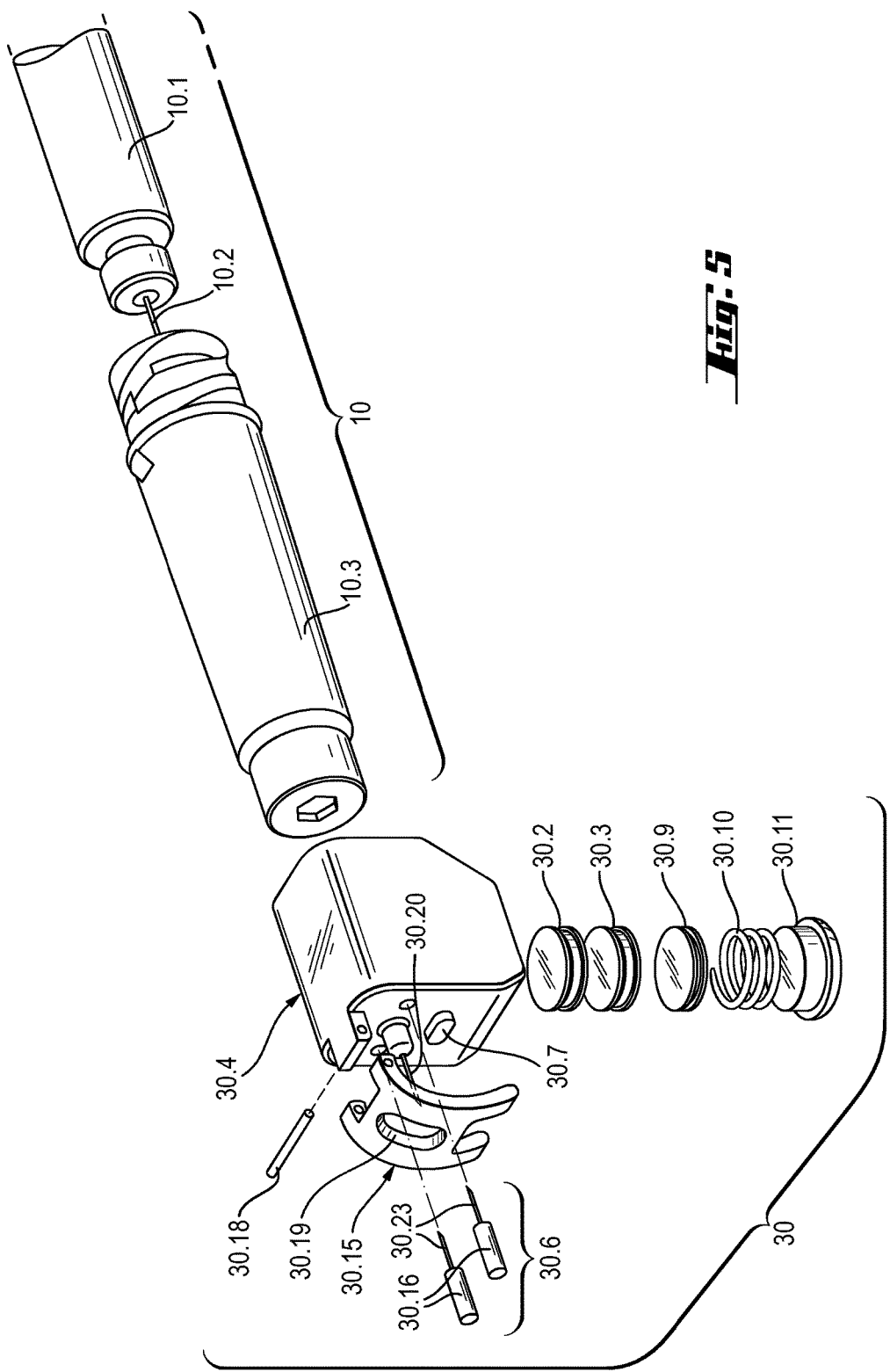
FIG. 5 is an exploded perspective view of another assembly according to the invention.

According to another embodiment an alternative locking mechanism is featured. FIG. 5 shows an exploded perspective view of this embodiment comprising a needle assembly housing 30.4, a reservoir, e.g. cylindrical bore 30.51, a locking plug 30.2, a moveable piston 30.3, a support member or support ring 30.9, an actuator, e.g. spring 30.10, and finally a closure 30.11 that closes the bore 30.51 to the outside.

The reservoir assembly 30.50 (see dotted-dashed line in FIG. 6) is part of a medicated needle assembly 30 that is attachable to an injection device, e.g. a pen-shaped injector 10 as described for the previous embodiment.

The needle assembly 30 comprises a housing 30.4 that is configured to attach to the injection device 10, e.g. instead of attaching a standard injection needle.

Figure 6:
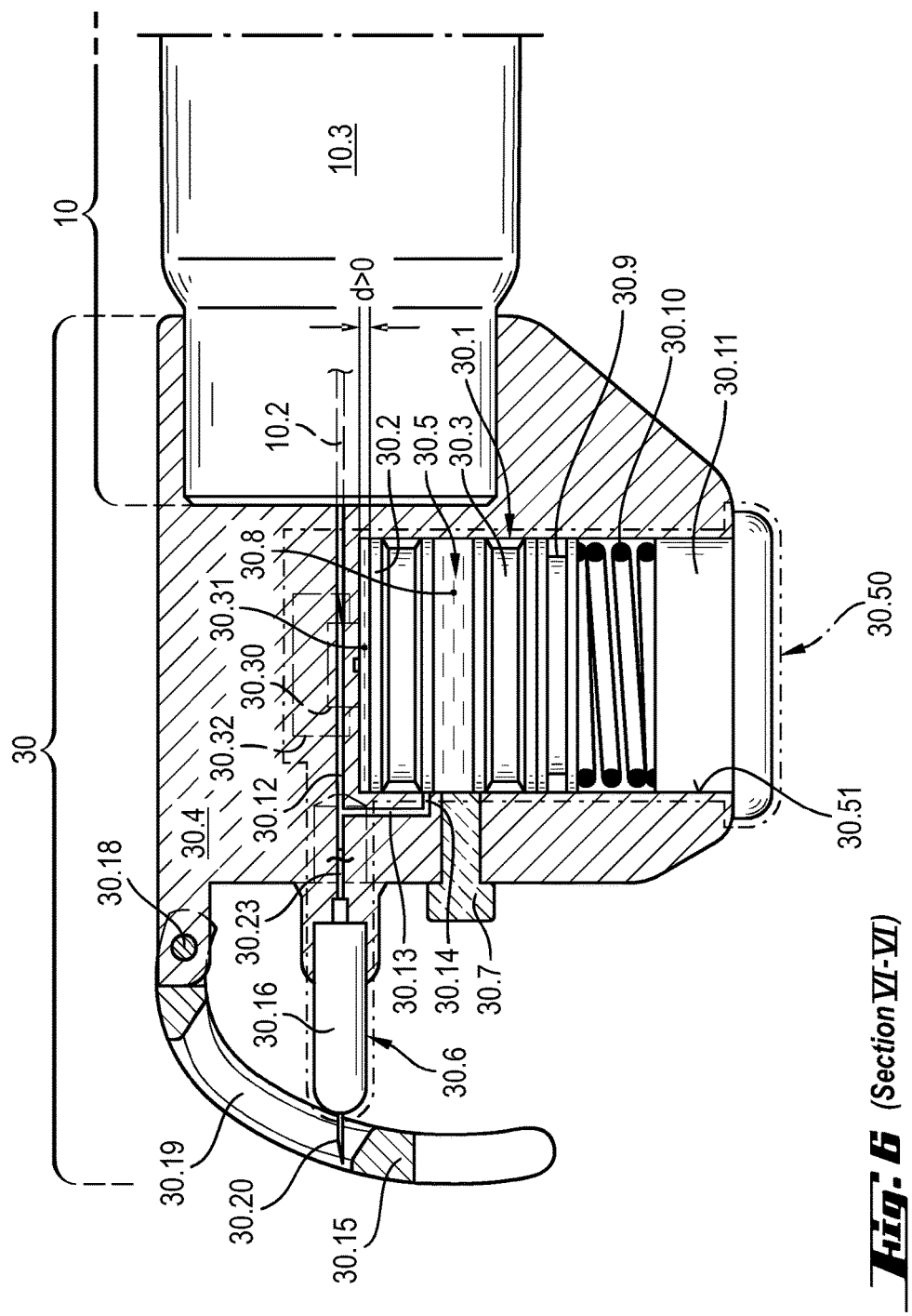
FIG. 6 is a side and partly section view of the assembly according to FIG. 5 and according to section VI-VI of FIG. 7.

As shown in FIG. 6, the housing 30.4 of the needle assembly 30 comprises a reservoir assembly 30.50 (dotted-dashed line) according to the present invention. A chamber or cavity, e.g. a cylindrical bore 30.51 is arranged inside the housing 30.4 accessible from the outside. The inner wall of the bore 30.51 defines a reservoir housing 30.1 containing (from inside to outside) a locking plug 30.2 and a movable piston 30.3, both arranged to be movable inside the cylindrical bore 30.51 and providing a fluid tight sealing with the inner wall of the bore 30.51. A reservoir cavity 30.5 is defined between the locking plug 30.2 and the movable piston 30.3 which is filled with medicament 30.8.

Next to the movable piston 30.3 is a support member or support ring 30.9, a spring 30.10, and finally a closure 30.11 that closes the bore to the outside. The reservoir housing 30.1 has a reservoir outlet 30.14. The reservoir assembly 30.50 further comprises an interlock 30.6 configured to prevent movement of the moveable locking plug 30.2 and/or the movable piston 30.3. The medicament 30.8 can be viewed from outside through an inspection glass 30.7.

The reservoir assembly 30.50 further comprises a head space 30.31 defined by the locking plug 30.2 and the housing 30.1. Moveable locking plug 30.2 is able to move a distance d into the head space 30.31 until it abuts the end of the cylindrical bore 30.51. Distance d is sufficient for locking plug 30.2 to open outlet 30.14 and fluidly connect the reservoir cavity 30.5 with the outlet 30.14.

FIG. 6 further shows fluid channel 30.12 arranged inside the housing 30.4 perpendicular to the reservoir housing 30.1 and extending from one end of the housing to the other end. When the needle assembly 30 is attached to an injection device 10, medicament from the injection device 10 can be discharged through the fluid channel 30.12. This could be used to prime the injection device 10 by removing air that might be present in the injection channel prior to injection. The fluid channel 30.12 then is fluidly connected to the medicament in the injection device 10 via needle 10.2, e.g. the needle could be attached to or part of the injection device 10.

Alternatively, the needle 10.2 could be part of the needle assembly 30 and in fluid communication with the fluid channel 30.12.

At the other end of the fluid channel 30.12 an injection needle 30.20 is fluidly connected.

A delivery or dispense channel 30.13 inside the needle assembly 30 is arranged to allow fluid communication between the fluid channel 30.12 and the medicament 30.8 inside the reservoir cavity 30.5 of the reservoir assembly 30.50. Depending on whether the reservoir outlet 30.14 is open or closed fluid communication is established or not. FIG. 6 shows the reservoir in a locked state, where the reservoir outlet 30.14 is closed or blocked by the movable locking plug 30.2. In this configuration, no fluid communication between the reservoir cavity 30.5 and the fluid channel 30.12 is established.

Figure 7:
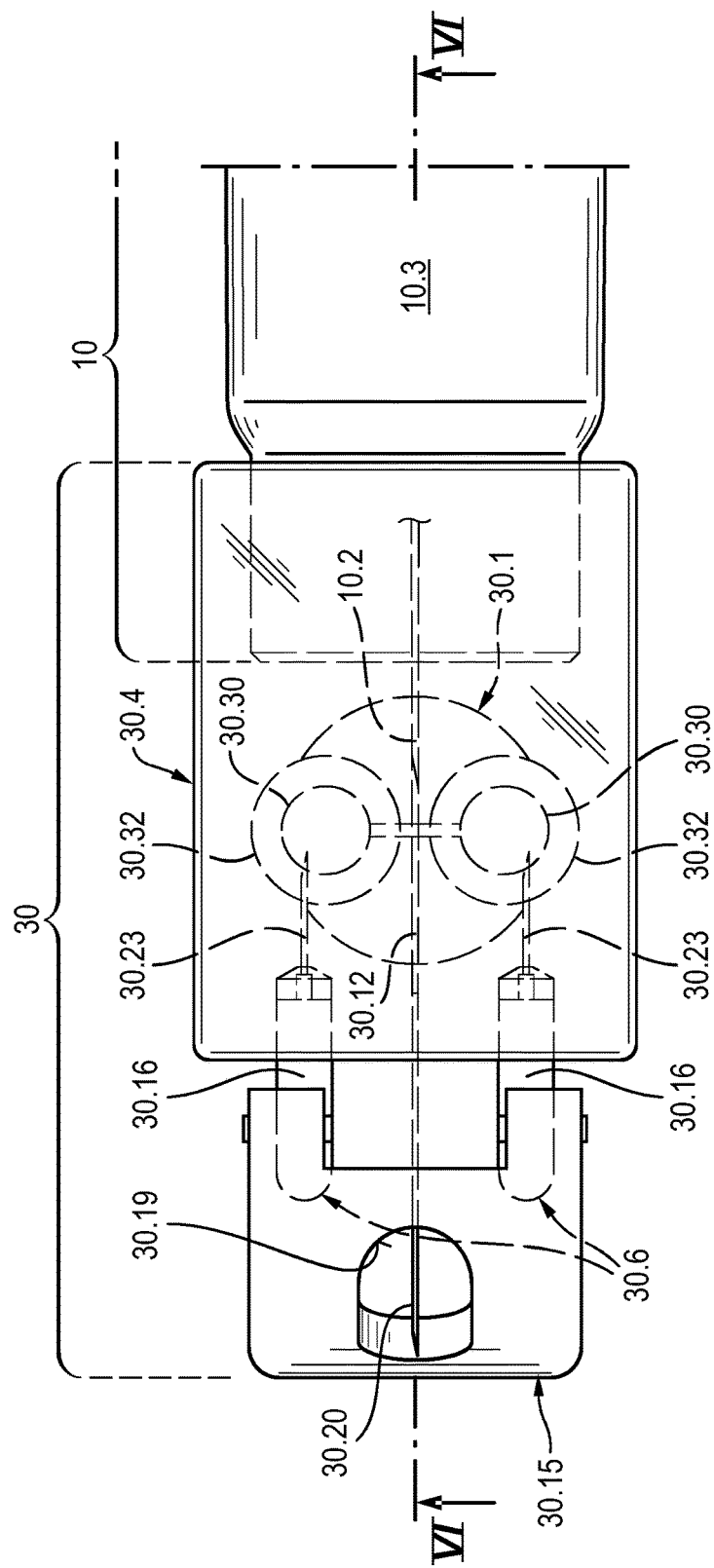
FIG. 7 is a top view of the assembly according to FIG. 5.

FIG. 7 is a top sectional view of the needle arrangement 30 showing the interlock 30.6. In this embodiment the interlock 30.6 comprises a slider having two legs 30.16 comprising a tappet 30.23 configured to pierce a membrane 30.30.

Membrane 30.30 separates the head space 30.31 filled with liquid from a sump 30.32. Headspace 30.31 is defined by the locking plug 30.2 and the reservoir housing 30.1. When the interlock 30.6 is in a first or locking position, the membrane 30.30 is intact, the head space 30.31 is filled with liquid and moveable locking plug 30.2 is prevented from movement. As stated before, in this position the movable locking plug seals or closes the reservoir outlet 30.14 (see FIG. 5). Hence, although biased by spring 30.10 the support ring 30.9 will remain in place and cannot be moved. Also, the movable piston 30.3 as well as the movable locking plug 30.2 is prevented to be moved.

When the interlock 30.6 is moved towards the arrangement housing 30.4, the tappets 30.23 at the end of legs 30.16 will pierce the membrane 30.30 and allow the liquid from the head space 30.31 to flow into the sump 30.32. While the head space 30.31 empties, locking plug 30.2 becomes free to be moved into the head space 30.31, caused by the biasing force of spring 30.10 acting on support member 30.9, moveable piston 30.3 and medicament 30.8. When interlock 30.6 is in the second or unlocked position, movable piston 30.3 as well as movable locking plug 30.2 is free to move.

In this embodiment, the interlock 30.6 comprises legs 30.16 having a tappet 30.23 configured to pierce membrane 30.30. Although the number of tappets may vary, the embodiment as described here features two tappets.

Alternatively, the interlock 30.6 could be configured to actuate a valve or valve system to close/open a fluid connection between the headspace 30.31 and the sump 30.32. For example, tappet 30.23 of slider 30.6 could be arranged to open a valve, when the interlock 30.6 is in unlocked position.

In either case, it is essential that when the interlock 30.6 is in locking position the liquid is prevented to flow from the head space 30.31 into the sump 30.32 and in unlocked position the liquid is allowed to flow from the head space 30.31 to the sump 30.32. Thus the interlock 30.6 is configured to prevent movement of the moveable locking plug 30.2 and/or the moveable piston 30.3.

A user could manually move interlock 30.6 from the locked position to the unlocked position. However, to improve usability, this embodiment features a lever 30.15 similar in construction as in the previous embodiment. The lever 30.15 has a concave curve towards the housing 30.4 of the needle assembly and is configured to act on the interlock 30.6 to be transitioned from a locked position to an unlocked position. The lever 30.15 is attached to the housing via a hinge 30.18 (see FIG. 8) at one end and abuts the interlock 30.6 at the other end. When the lever 30.15 is moved towards the housing 30.4 the interlock 30.6 will be pushed towards the housing 30.4 such that the tappets 30.23 pierce the membrane. Hence, lever 30.15 is configured to change the status of the interlock 30.6 from locked to unlocked.

Figure 8:
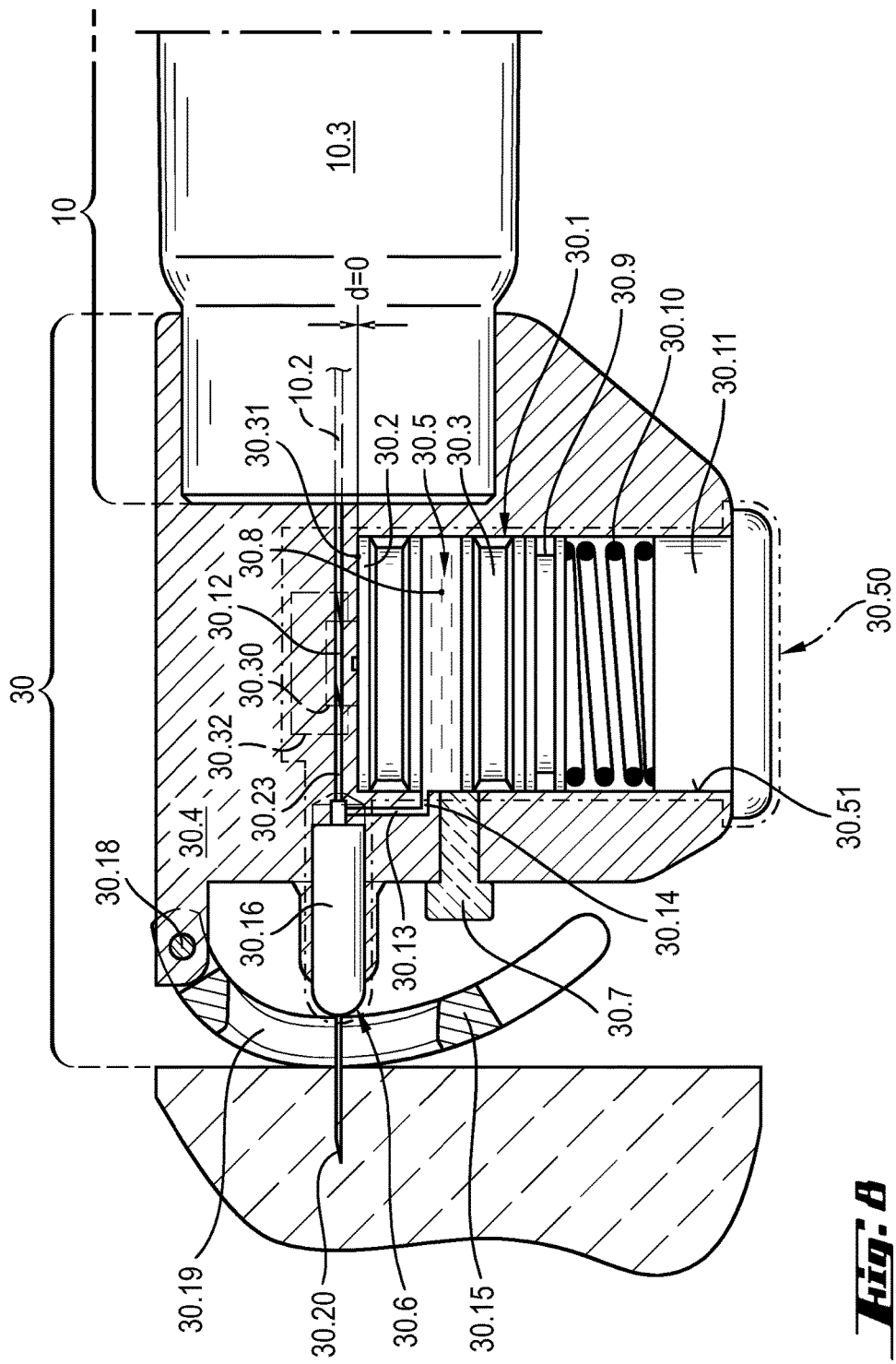

FIG. 8 shows a sectional side view of the needle arrangement 30 where the lever 30.15 is fully depressed and the interlock 30.6 is in an unlocked state. The membrane 30.30 is pierced and moveable locking plug 30.2 is free to move caused by the biasing force of spring 30.10 as described above. As spring 30.10 acts on the support ring 30.9, support ring 30.9, moveable piston 30.3, medicament 30.8, and moveable locking plug 30.2 will be moved. Moveable locking plug 30.2 is able to move a distance d (see FIG. 8) until it abuts the end of the cylindrical bore 30.51. In the position shown in FIG. 8, moveable locking plug 30.2 has moved into head space 30.31, distance d is zero, outlet 30.14 is open, and reservoir cavity 30.5 is fluidly connected with outlet 30.14.

Alternatively, the bore 30.51 could comprise a step, detent, or the like structure, such that locking plug 30.2 is able to move distance d into the head space 30.31 to open outlet 30.14 before abutting the step, detent, or the like structure.

As further alternative, the volume of the sump 30.32 could be configured to define distance d. When sump 30.32 is filled with liquid from head space 30.31 distance d becomes zero and locking plug 30.2 is moved such that outlet 30.14 is open and fluidly connected with reservoir cavity 30.5.

Returning to FIG. 8, as spring 30.10 still presses against support ring 30.9 and movable piston 30.3, medicament 30.8 will be pushed out the reservoir cavity 30.5 through reservoir outlet 30.14, into dispense channel 30.13 and into liquid channel 30.12. Dispense will end when moveable piston 30.3 abuts moveable locking plug 30.2.

As in the embodiment of needle arrangement 20 described before, lever 30.15 is configured such that it protects against potential needle stick or reduces needle phobia. For this purpose, lever 30.15 has a cutout 30.19, e.g. of oval shape, to allow an injection needle 30.20 to pass through. Before injection, the injection needle 30.20 tip is shielded by lever 30.15. During injection, a user presses the needle arrangement 30 against an injection site and while lever 30.15 is depressed against the housing 30.4 of the needle arrangement the injection needle 30.20 would extend through the cutout 30.19 and enter the injection site.

As lever 30.15 is depressed the state of the interlock 30.6 is changed and needle arrangement 30 is actuated. Medicament from the needle arrangement 30 is dispensed without the user having to perform a further injecting action, such as depressing a plunger or the like. After the medicament 30.8 is discharged the user may dispense medicament form the attached drug delivery device in a usual manner. The two medicaments are dispensed subsequently one after the other, without substantial mixing in the devices.

Again, according to the construction of the needle assembly 30, the dispense channel 30.13 and the liquid channel 30.12 are configured to minimize ullage and thus help the user to receive the required amount of medicament without wasting medicament.

The skilled person will be aware of alternative needle shields, for instance tubular shaped shields or telescoping shields. Further, the skilled person will be aware of alternative interlocks, such as bolts, clamps, notches or the like. All such alternatives are within the scope of this invention unless they are precluded by the language of the claims.

The invention has been described in terms of a needle assembly comprising a reservoir assembly. However, the skilled person will immediately understand that the concept of the inventive reservoir assembly can be readily applied to other kinds of reservoir assemblies, such as ampoules, cartridges, bag or bellow-type of flexible reservoirs. It is also clear to the skilled person that the inventive concept can be readily applied to other kinds of medical devices.

The invention claimed is:

1. A reservoir assembly comprising:
   a reservoir housing, a piston, and a locking plug, both movably arranged inside the reservoir housing, wherein the volume between the piston and the locking plug defines a reservoir cavity;
   a reservoir outlet;
   a biased actuator configured to act on the piston; and
   an interlock configured to prevent movement of at least one of the locking plug and the piston, the interlock having a locked position and an unlocked position,
   wherein the locking plug is configured to be movable from a first position, when the interlock is in the locked position, to a second position, when the interlock is in the unlocked position, wherein in the first position the reservoir outlet is not in fluid communication with the reservoir cavity and in the second position the reservoir outlet is in fluid communication with the reservoir cavity,
   wherein when the interlock is in the locked position the locking plug seals the reservoir outlet,
   wherein when the interlock is in the unlocked position the locking plug is free to move and actuation of the piston by the actuator causes movement of the locking plug, and
   wherein the actuator comprises a spring and a support ring arranged between the spring and the piston, the support ring configured to exert a force onto the piston.

2. A reservoir assembly according to claim 1, wherein when the interlock is in the unlocked position and the locking plug is in the second position, the reservoir outlet is in fluid communication with the reservoir cavity.

3. A reservoir assembly according to claim 1, wherein the reservoir cavity is filled with medicament.

4. A reservoir assembly according to claim 1, further comprising a head space defined by the locking plug and the reservoir housing, wherein when the locking plug is moved into the head space, the locking plug is in the second position.

5. A reservoir assembly according to claim 1, wherein the interlock comprises a movable slider, the slider having an aperture, wherein the slider can be moved from a first position to a second position, such that the support ring can pass through the aperture.

6. A reservoir assembly according to claim 5, wherein when the slider is in a position where the support ring can pass through the aperture the actuator can act on the piston and the locking plug is movable into the second position, so that the reservoir outlet is in fluid communication with the reservoir cavity.

7. A medical device configured for delivering a medicament comprising a reservoir assembly of claim 1.

8. A needle assembly attachable to an injection device, the needle assembly comprising a housing having a proximal end and a distal end, wherein the proximal end is configured to be attached to an injection device; wherein a distal injection needle is fixed at the housing; the housing comprising a reservoir assembly according to claim 1; and wherein the reservoir assembly is configured for fluid communication with the distal injection needle.

9. The needle assembly of claim 8, wherein the reservoir assembly is in fluid communication with the distal injection needle when the interlock is in the unlocked position.

* * * * *